(12) United States Patent
Green et al.

(10) Patent No.: US 10,043,645 B2
(45) Date of Patent: Aug. 7, 2018

(54) METHOD OF LOCALIZING LIPID DOUBLE BONDS

(71) Applicant: MICROMASS UK LIMITED, Wilmslow (GB)

(72) Inventors: Martin Raymond Green, Bowdon (GB); Keith Richardson, High Peak (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/304,634

(22) PCT Filed: Apr. 14, 2015

(86) PCT No.: PCT/GB2015/051126
§ 371 (c)(1),
(2) Date: Oct. 17, 2016

(87) PCT Pub. No.: WO2015/159063
PCT Pub. Date: Oct. 22, 2015

(65) Prior Publication Data
US 2017/0047211 A1 Feb. 16, 2017

(30) Foreign Application Priority Data
Apr. 17, 2014 (GB) .................................. 1406992.6
Apr. 22, 2014 (EP) .................................. 14165455

(51) Int. Cl.
*H01J 49/00* (2006.01)
*G01N 33/92* (2006.01)
*G01B 15/00* (2006.01)

(52) U.S. Cl.
CPC .......... *H01J 49/0059* (2013.01); *G01B 15/00* (2013.01); *G01N 33/92* (2013.01); *H01J 49/0031* (2013.01)

(58) Field of Classification Search
CPC ............... H01J 49/0027; H01J 49/0031; H01J 49/0059; H01J 49/0045; G01N 33/92; G01B 15/00
See application file for complete search history.

(56) References Cited

U.S. PATENT DOCUMENTS 7,771,943 B2   8/2010   Blanksby et al.
9,123,523 B2   9/2015   Green et al.
(Continued)

FOREIGN PATENT DOCUMENTS

WO    2013/173642    11/2013

OTHER PUBLICATIONS

Pham et al, "Rapid Differentiation of Isomeric Lipids by Photodissociation Mass Spectrometry of Fatty Acid Derivatives", Rapid Commun. Mass Spectrom. 2013, 27, 805-813.*
(Continued)

*Primary Examiner* — David E Smith
(74) *Attorney, Agent, or Firm* — Womble Bond Dickinson (US) LLP; Deborah M. Vernon; Heath T. Misley

(57) ABSTRACT

A method of mass spectrometry for analyzing lipids and similar biological molecules is disclosed. The lipid molecules may be ionized to form a plurality of lipid parent ions and subjected to photon-induced fragmentation to form a plurality of fragment or product ions. The position of one or more unsaturated bonds in the lipid molecules may be determined by mass analyzing the fragment and product ions and analyzing their intensity profile.

18 Claims, 5 Drawing Sheets

(56) References Cited

U.S. PATENT DOCUMENTS

| | | | | |
|---|---|---|---|---|
| 2008/0296486 A1* | 12/2008 | Blanksby | ............ | H01J 49/0045 250/282 |
| 2009/0194682 A1* | 8/2009 | Zhang | ................ | G01N 33/6848 250/282 |
| 2010/0276583 A1* | 11/2010 | Senko | .................. | H01J 49/427 250/282 |
| 2014/0224974 A1* | 8/2014 | Kenny | ................ | H01J 49/0059 250/282 |
| 2015/0144780 A1* | 5/2015 | Brown | ................ | H01J 49/0072 250/282 |
| 2016/0314952 A1 | 10/2016 | Giuliani et al. | | |

OTHER PUBLICATIONS

Devakumar et al, "Structural Analysis of Leukotrine C4 Isomers Using Collisional Activation and 157 nm Photodissociation", J. Am. Soc. Mass Spectrom 2008, 19, 14-26.*

Zucker et al, "An Ion Mobility/Ion Trap/Photodissociation Instrument for Characterization of Ion Structure", J. Am. Mass Spectrom. (2011) 22:1477-1485.*

Antione et al, "Electron Photodetachment Dissociation for Structural Characterization of Synthetic and Biopolymer Anions", Mass Spectrometry Reviews, vol. 33 Issue 6, 2013.*

Pham et al, "Rapid Differentiation of Isomeric Lipids by Photodissociation Mass Spectrometry of Fatty Acid Derivatives", Rapid Commun. Mass Spectrom.,2013, 27, 805-815.*

O Brien et al, 193 nm Ultraviolet Photodissociation Mass Spectrometry for the Structural Elucidation of Lipid A Compounds in Complex Mixtures, Analytical Chemistry 2014, 86, 2138-2145.*

Devakumar et al, "Structural Analysis of Leukotriene C4 Isomers Using Collisional Activation and 157 nm Photodissociation", J. Am. Soc. Mass Spectrom 2008, 19, 14-26.*

Devakumar et al., "Structural Analysis of Leukotriene C4 Isomers Using Collisional Activation and 157 nm Photodissociation", Journal of the American Society for Mass Spectrometry, Elsevier Science Inc., US., vol. 19, No. 1, pp. 14-26, Jan. 2008.

John P. O'Brien et al., "Structural Characterization of Gangliosides and Glycolipids via Ultraviolet Photodissociation Mass Spectrometry", Analytical Chemistry, vol. 85, No. 21, pp. 10399-10407, Nov. 2013.

John P. O'Brien et al., "193 nm Ultraviolet Photodissociation Mass Spectrometry for the Structural Elucidation of Lipid a Compounds in Complex Mixtures" Analytical Chemistry, vol. 86, No. 4, pp. 2138-2145, Feb. 2014.

Huong T. Pham et al., "Rapid Differentiation of Isomeric Lipids by Photodissociation Mass Spectrometry of Fatty Acid Derivatives", Rapid Communications in Mass Spectrometry, vol. 27, No. 7, pp. 805-815, Apr. 2013.

Zucker S M et al., "An Ion Mobility/Ion Trap/Photodissociation Instrument for Characterization of Ion Structure", Journal of the American Society for Mass Spectrometry, Elsevier Science Inc., US., vol. 22, No. 9, pp. 1477-1485, Sep. 2011.

Thomas et al., "Ozonolysis of Phospholipid Double Bonds During Electrospray Ionization: A New Tool for Structure Determination", J. Am. Chem. Soc., vol. 128, No. 1, pp. 58-59, 2006.

Hsu et al., "Structural Determination of Sphingomyelin by Tandem Mass Spectrometry with Electrospray Ionization", J. Am. Soc. Mass Spectrom., vol. 11, pp. 437-449, 2000.

Cook et al., "Metastable Atom-Activated Dissociation Mass Spectrometry: Leucine/Isoleucine Differentiation and Ring Cleavage of Proline Residues", J. Mass Spectrom., vol. 44. pp. 1211-1223, 2009.

Green et al., "Investigation into UV Photon-Induced Fragmentation in a RF Confined Ion Guide Using a Commercial Vaccum UV Ionisation Lamp" May 2013.

* cited by examiner

METHOD OF LOCALIZING LIPID DOUBLE BONDS

CROSS-REFERENCE TO RELATED APPLICATIONS

This application represents a National Phase of International Application No. PCT/GB2015/051126 entitled "Method of Localizing Lipid Double Bonds" filed 14 Apr. 2015, which claims priority from and the benefit of United Kingdom Patent Application No. 1406992.6 filed 17 Apr. 2014, and European Patent Application No. 14165455.8 filed 22 Apr. 2014. The entire contents of these applications are incorporated herein by reference.

FIELD OF THE INVENTION

The present invention relates generally to mass spectrometry and in particular to methods of mass spectrometry and mass spectrometers.

BACKGROUND

Biological lipid molecules consist of a polar structure (head group) and one or more non polar hydrocarbon chains. The hydrocarbon chains may contain one or more unsaturated C—C bonds. The number and position of these unsaturated bonds has a significant implication for biological activity.

It is known to use an Electrospray ion source in positive ion mode to ionise lipids and other biomolecules to form $[M+H]^+$ singly charged molecular cations. The molecular cations may then be subjected to Collision Induced Dissociation ("CID") so as to form a plurality of fragment ions. However, the resulting MS-MS mass spectra tend to be dominated by fragment ions associated with the polar head group of the lipid molecules and disadvantageously no structural information as to the position of the unsaturated bonds on the hydrocarbon chains is available.

The standard conventional approach involving using Collision Induced Dissociation is therefore unable to provide structural information as to the position of unsaturated bonds in lipids and other biomolecules. WO 2013/173642 (Sanford-Burnham Medical Research Institute) describes a high-throughput CID lipidomics technique.

Various attempts have been made to try to provide information relating to the location of e.g. double bonds in biological molecules.

US 2008/0296486 (Blanksby) describes a method for the determination of the position of unsaturation in a compound involving isolating a precursor ion and causing it to react with ozone. The position of unsaturation is determined using the mass difference between the isolated ion and an ozone-induced fragment ion.

H. T. Pham, A. J. Trevitt, T. W. Mitchell and S. J. Blanksby "Rapid differentiation of isomeric lipids by photodissociation mass spectrometry of fatty acid derivatives" Rapid Communications in Mass Spectrometry, 27(7), p. 805-815 (2013) discloses the derivatization of a structurally diverse suite of fatty acids as 4-iodobenzyl esters. Electrospray ionisation of these derivatives in the presence of sodium acetate yields abundant $[M+Na]^+$ ions that can be mass selected and subjected to laser irradiation at a wavelength of 266 nm.

A. Devakumar, D. K. O'Dell, J. Michael Walker and J. P. Reilly "Structural Analysis of Leukotriene $C_4$ Isomers Using Collisional Activation and 157 nm Photodissociation" American Society for Mass Spectrometry, vol. 19, no. 1 (2008) discloses the use of laser photodissociation as part of the structural characterisation of the two $LTC_4$ isomers. Other laser photodissociation structural analyses are described in J. P. O'Brien and J. S. Brodbelt "Structural Characterisation of Gangliosides and Glycolipids via Ultraviolet Photodissociation Mass Spectrometry" Anal. Chem., 85, 10399-10407 (2013) and J. P. O'Brien, B. D. Needham, J. C. Henderson, E. M. Nowicki, M. Stephen Trent and J. S. Brodbelt "193 nm Ultraviolet Photodissociation Mass Spectrometry for the Structural Elucication of Lipid A Compounds in Complex Mixtures" Anal. Chem., 86, 2138-2145 (2014).

M. C. Thomas, T. W. Mitchell and S. J. Blanksby "Ozonolysis of Phospholipid Double Bonds during Electrospray Ionization: A New Tool for Structure Determination" J. Am. Chem. Soc. 128(1), p. 58-59 (2006) discloses ozonolysis of double bonds during the negative ion electrospray ionization of unsaturated phospholipids under conditions that produce a corona discharge. Ionic products of the ozonolysis are detected and characterised by mass spectrometry.

F. Hsu and J. Turk "Structural determination of sphingomyelin by tandem mass spectrometry with Electrospray ionization", J. Am. Soc. Mass Spectrom., 11, p. 437-449 (2000) discloses forming alkaline metal adduct ions of sphingomyelin by Electrospray ionization.

S. L. Cook, O. L. Collin and G. P. Jackson "Metastable atom-activated dissociation mass spectrometry: leucine/isoleucine differentiation and ring cleavage of proline residues." J. Mass. Spectrom., 44, p. 1211-1223 (2009) discloses extensive backbone fragmentation resulting in a-, b-, c-, x-, y- and z-type ions of singly and doubly charged peptide ions through their interaction with a high kinetic energy beam of argon or helium metastable atoms.

M. Green, K. Richardson, J. Brown and P. Murray "Investigation into UV photon-induced fragmentation in a RF confined ion guide using a commercial vacuum UV ionisation lamp" Poster ASMS May 2013 discloses using a UV lamp to fragment ions.

WO 2013/171495 (Micromass) discloses a mass spectrometer comprising a photoionisation device for excitation of reagent molecules within an RF ion guide.

WO 2013/021124 (Giuliani) discloses using a glow discharge lamp to fragment ions trapped in an ion trap.

Several of the known methods suffer from the serious disadvantage that the lipid molecules must first be derivatised or reacted with a separate reagent before analysis.

Several of the known methods suffer from the problem that the efficiency of the process is very low.

It is therefore desired to provide an improved method of mass spectrometry and in particular to provide an improved method of mass spectrometry to determine the location of double bonds in lipids.

SUMMARY

According to an aspect there is provided a method of mass spectrometry comprising:

ionising lipid molecules to form a plurality of lipid parent ions;

subjecting the lipid parent ions to photon-induced fragmentation in order to cause the lipid parent ions to fragment to form a plurality of fragment or product ions;

mass analysing the fragment or product ions; and determining the position of one or more unsaturated bonds in the lipid molecules by analysing an intensity profile of fragment or product ions that correspond with cleavage of carbon-carbon bonds from the end of a hydrocarbon chain of the lipid up to the position of an unsaturated bond within the chain.

The techniques described herein relate to new methods of localization of unsaturated or double bonds in (e.g.) lipid molecules.

Photon-induced fragmentation allows cleavages of carbon-carbon bonds along a hydrocarbon chain to be probed. It has been recognised that the resulting intensity profile of the fragments corresponding to cleavage of carbon-carbon bonds along a hydrocarbon chain containing an unsaturated bond up to the position of the unsaturated bond is characteristic of the position of the bond within the chain. Analysing the intensity profile of these fragment or product ions thus allows the position of unsaturated bonds to be elucidated.

In particular, the intensity profile may be a characteristic envelope containing one or more peaks corresponding to one or more carbon-carbon bond cleavages along the hydrocarbon chain.

The photon-induced fragmentation may generally be radical driven. That is, the fragmentation may proceed via one or more radical or metastable precursor or product ions. Particularly, the step of subjecting the parent ions to photon-induced fragmentation may form a doubly charged radical precursor ion. This means that the fragmentation is stochastic in nature and may result in bond cleavages that would not occur e.g. through using conventional Collisional Induced Dissociation ("CID") fragmentation. The photon-induced fragmentation thus allows the carbon-carbon bonds along the hydrocarbon chain to be directly probed. The photon-induced fragmentation may comprise illuminating the lipid parent ions with high energy photons e.g. in the ultraviolet range.

The fragment or product ions may be multiply or substantially doubly charged.

Generally, the fragmentation will result in a mixture of fragment ions of different charge states. However, it has been found that the higher charge state fragment ions formed via photon-induced fragmentation processes are of particular utility for elucidating bond position.

Optionally, no derivatisation of the compound prior to fragmentation is required.

The method may involve the use of a simple and inexpensive incoherent or non-laser light source such as an ultra-violet ("UV") lamp rather than a relatively expensive laser in order to induce fragmentation of lipid parent ions and/or other ions of biological origin.

In particular, it has been shown that when positive singly charged phospholipid ions are exposed to high energy UV radiation then photon induced electron detachment may occur. This process may occur in a direct manner or via interaction with excited neutrals. The process generally results in the formation of a radical doubly charged ion which then fragments to form an envelope of doubly charged fragment or product ions. The fragment or product ions can be assigned to a series of C—C bond cleavages from the end of the hydrocarbon chains of the lipid up to the position of a double bond within the chain.

The parent ions may be caused to fragment via photon induced electron detachment. This may form a radical doubly charged precursor ion.

The fragmentation process may involve the loss of hydrocarbon chain subunits directly from intact doubly charged radical molecular cations. This process is not available by Collision Induced Dissociation as no doubly charged radical ions are formed.

The techniques described herein are concerned with methods of using the fragment ion information in the spectrum produced by UV photon induced electron detachment to elucidate double bond position.

Lipid molecules are generally bio-molecules, organic molecules or biological molecules. The lipid molecules may comprise one, two or more than two alkyl chains.

The lipid molecules may comprise one or more triglycerols, glycerophospholiids, sphingolipids, fatty acids, glycerolipids or saccharolipids.

The method may further comprise confining the lipid parent ions in an ion guide whilst subjecting the lipid parent ions to photon-induced fragmentation.

The ion guide may comprise an RF ion guide.

The method may further comprises using a RF pseudo-potential to confine ions within the ion guide.

The lipid parent ions generally comprise a first charge state. The fragment or product ions may comprise a second different charge state.

The second charge state may be a higher positive charge state or more positive than the first charge state. For example, the first charge state may be singly positively charged and the second charge state may be doubly positively charged. Alternatively, the first charge state may be doubly negatively charged and the second charge state may be singly negatively charged (i.e. more positive even though the charge number z appears lower).

The lipid parent ions may be substantially singly charged.

The fragment or product ions may be substantially doubly charged.

The step of subjecting the lipid parent ions to photon-induced fragmentation may cause the lipid parent ions to fragment directly.

The step of subjecting the lipid parent ions to photon-induced fragmentation may cause the lipid parent ions to fragment by photon induced electron detachment, photodissociation or photo-activation.

The step of subjecting the lipid parent ions to photon-induced fragmentation may cause the lipid parent ions to fragment indirectly.

The method may further comprise causing at least some of the lipid parent ions to interact with excited neutral gas molecules.

The method may further comprise causing at least some of the lipid parent ions to form radical ions and/or metastable ions.

The radical ions and/or metastable ions may subsequently dissociate to form the fragment or product ions.

The step of subjecting the lipid parent ions to photon-induced fragmentation may comprise subjecting the lipid parent ions to ultraviolet radiation.

The step of subjecting the lipid parent ions to photon-induced fragmentation comprise directing photons emitted from a vacuum ultraviolet ("VUV") discharge lamp, a glow discharge lamp, an ultraviolet lamp, a lamp, an incoherent light source or non-laser light source onto the lipid parent ions.

The photons may have an energy selected from the group consisting of: (i) < about 1 eV; (ii) about 1-2 eV; (iii) about 2-3 eV; (iv) about 3-4 eV; (v) about 4-5 eV; (vi) about 5-6 eV; (vii) about 6-7 eV; (viii) about 7-8 eV; (ix) about 8-9 eV; (x) about 9-10 eV; (xi) about 10-11 eV; (xii) about 11-12 eV; (xiii) about 12-13 eV; (xiv) about 13-14 eV; (xv) about 14-15 eV; (xvi) about 15-16 eV; (xvii) about 16-17 eV; (xviii) about 17-18 eV; (xix) about 18-19 eV; (xx) about 19-20 eV; (xxi) about 20-21 eV; (xxii) about 21-22 eV; (xxiii) about 22-23 eV; (xxiv) about 23-24 eV; (xxv) about 24-25 eV; (xxvi) about 25-26 eV; (xxvii) about 26-27 eV; (xxviii) about 27-28 eV; (xxix) about 28-29 eV; (xxx) about 29-30 eV; (xxxi) about 30-31 eV; (xxxii) about 31-32 eV; (xxxiii) about 32-33 eV; (xxxiv) about 33-34 eV; (xxxv) about 34-35 eV; (xxxvi) about 35-36 eV; (xxxvii) about 36-37 eV; (xxxviii) about 37-38 eV; (xxxix) about 38-39 eV; (xl) about 39-40 eV; and (xli) > about 40 eV.

The photons may have an wavelength selected from the group consisting of: (i) about 30-50 nm; (ii) about 50-100 nm; (iii) about 100-150 nm; (iv) about 150-200 nm; (v) about 200-250 nm; (vi) about 250-300 nm; (vii) about 300-350 nm; and (viii) about 350-400 nm.

The step of analysing the intensity profile of the fragment or product ions in order to determine the position of one or more bonds in the lipid molecules may comprise comparing the intensity profile to one or more previous experimentally obtained intensity profiles.

The step of analysing the intensity profile of the fragment or product ions in order to determine the position of one or more bonds in the lipid molecules comprise comparing the intensity profile to a predicted, calculated or theoretical intensity profile.

The step of analysing the intensity profile of the fragment or product ions in order to determine the position of one or more bonds in the lipid molecules may comprise determining the position of one or more C=C double bonds, carbon double bonds or vinyl bonds in the lipid molecules.

The method may further comprise subjecting at least some of the lipid parent ions or the plurality of fragment or product ions to supplementary activation to form a plurality of further fragment or product ions and mass analysing the further fragment or product ions.

The method may further comprise selecting by mass or using a mass filter one or more of the lipid parent ions or one or more ions derived from the lipid parent ions prior to the step of supplementary activation.

The method may further comprise separating at least some of the lipid parent ions, at least some ions derived from the lipid parent ions or at least some fragment or product ions according to ion mobility prior to mass analysis.

According to another aspect there is provided a mass spectrometer comprising:

an ion source arranged and adapted to ionise lipid molecules to form a plurality of lipid parent ions;

a photon-induced fragmentation device arranged and adapted to subject the lipid parent ions to photon-induced fragmentation in order to cause the lipid parent ions to fragment to form a plurality of fragment or product ions;

a mass analyser arranged and adapted to mass analyse the fragment or product ions; and a control system arranged and adapted to analyse an intensity profile of the fragment or product ions in order to determine the position of one or more bonds in the lipid molecules.

According to another aspect there is provided a method of mass spectrometry comprising:

ionising first molecules to form a plurality of first parent ions;

subjecting the first parent ions to photon-induced fragmentation in order to cause the first parent ions to fragment to form a plurality of fragment or product ions;

mass analysing the fragment or product ions; and analysing an intensity profile of the fragment or product ions in order to determine the position of one or more bonds in the first molecules, wherein the first molecules comprise one or more bio-molecules.

The bio-molecules may comprise one or more alkyl chains containing an unsaturated double bond. Determining the position of the one or more bonds in the first molecule may comprise determining the position of one or more unsaturated bonds within the alkyl or hydrocarbon chain by analysing an intensity profile of fragment or product ions that correspond with cleavage of carbon-carbon bonds from the end of the alkyl or hydrocarbon chain up to the position of the unsaturated bond.

For instance, the bio-molecules may comprise lipids, hydrocarbons, vegetable oils, fatty acids, fatty aldehydes or ketones.

The method of this aspect is compatible with and may be combined with any or all of the features described in relation to any of the aspects to the extent that they are not mutually exclusive. In particular, it will be appreciated that the features described above and not limited to use for analysis of lipids and may equally be used to analyse e.g. hydrocarbons, vegetable oils, fatty acids, fatty aldehydes or ketones.

According to another aspect there is provided a mass spectrometer comprising:

an ion source arranged and adapted to ionise first molecules to form a plurality of first parent ions;

a photon-induced fragmentation device arranged and adapted to subject the first parent ions to photon-induced fragmentation in order to cause the first parent ions to fragment to form a plurality of fragment or product ions;

a mass analyser arranged and adapted to mass analyse the fragment or product ions; and a control system arranged and adapted to analyse an intensity profile of the fragment or product ions in order to determine the position of one or more bonds in the first molecules, wherein the first molecules comprise one or more bio-molecules.

According to another aspect there is provided a method of mass spectrometry comprising:

ionising first molecules to form a plurality of parent ions;

subjecting the parent ions to photon-induced fragmentation to form a plurality of second ions;

separating at least some of the second ions according to ion mobility;

mass analysing the at least some second ions or ions derived from the at least some second ions; and determining the structure of the molecules by analysing an intensity and ion mobility separation profile of the at least some second ions or of the ions derived from the at least some second ions, wherein the first molecules comprise bio-molecules comprising one or more alkyl chains comprising an unsaturated bond.

It has been found that ion mobility separation of the fragment ions gives patterns that are highly indicative of the point at which the alkyl chains have been cleaved. This essentially gives a 3D fingerprint of the molecule which can be powerful method for identifying the analyte molecule. For instance, where the bio-molecule contains two or more alkyl chains, cleavage of carbon-carbon bonds at different positions along the two chains may give rise to fragment ions having the same mass to charge ratio. However, these fragment ions would have different structures and may be separated by ion mobility.

This technique may be of particular interest for lipid molecules where many of the fragments may have the same mass to charge ratio but quite different structures. However, it will be appreciated that the technique will also provide advantages for many other types of analysis.

Analysing the intensity profile may comprise determining the position of one or more unsaturated bonds in the molecules by analysing an intensity profile of fragment or product ions that correspond with cleavage of carbon-carbon bonds from the end of a hydrocarbon chain of the lipid up to the position of an unsaturated bond within the chain.

The step of photon-induced fragmentation is generally similar to that described above in relation to the first aspect, and the skilled person will understand any or all features described in relation to the first aspect also apply to this aspect, to the extent that they are not mutually incompatible. In particular, the step of photon-induced fragmentation may cause the parent ions to undergo photon-induced electron detachment to form multiply or doubly charged radical precursor ions.

The method may further comprise subjecting the second ions to supplementary activation, optionally wherein the supplementary activation comprises collisional induced dissociation. Collisional induced dissociation of the radical or metastable precursor ions (e.g. formed via electron detachment) may allow direct cleavage of the carbon-carbon bonds.

The method may further comprise selecting one or more of the second ions according to mass or using a mass filter prior to the step of subjecting the second ions to supplementary activation and/or prior to separating the second ions according to ion mobility, wherein the method optionally further comprises the step of mass analysing the second ions which have been subjected to supplementary activation.

The second ions may comprise one or more radical and/or metastable precursor ions.

These may be formed e.g. via electron detachment. Generally, the step of photon-induced fragmentation will also form a plurality of fragment or product ions. The radical and/or metastable precursor ions may be multiply e.g. doubly charged. At least some of the fragment or product ions may also be multiply e.g. doubly charged.

The method may comprise:
selecting one or more of the radical and/or metastable precursor ion by mass or using a mass filter;
subjecting the selected radical and/or metastable precursor ion to supplementary activation to form a plurality of further fragment or product ions;
separating the further fragment or product ions according to ion mobility;
mass analysing the further fragment or product ions; and
determining the structure of the molecules by analysing an intensity and ion mobility separation profile of further fragment or product ions.

The first molecules may comprise lipids. The first molecules may also comprise hydrocarbons, vegetable oils, fatty acids, fatty aldehydes or ketones.

According to another aspect there is provided a mass spectrometer comprising:
an ion source arranged and adapted to ionise first molecules to form a plurality of first parent ions;
a photon-induced fragmentation device arranged and adapted to subject the first parent ions to photon-induced activation or fragmentation;
an ion mobility separation device for separating ions according to ion mobility;
a mass analyser arranged and adapted to mass analyse ions; and
a control system arranged and adapted to determine the structure of the molecules by analysing an intensity and ion mobility separation profile of the ions.

The mass spectrometer may further comprise a supplementary activation device, optionally wherein the supplementary activation device comprises a collision cell arranged and adapted to cause ions to undergo collisional induced dissociation.

The mass spectrometer may further comprise a mass filter.

The mass filter may be disposed between photon-induced fragmentation device and the ion mobility separation device. Alternatively, the mass filter may comprise part of the photon-induced fragmentation device.

According to another aspect there is provided a method of mass spectrometry comprising:
ionising a lipid molecule to form a molecular ion;
subjecting the ion to VUV radiation with an energy range such that intact radical precursor ions or fragment ions from the precursor with a more positive charge state than the original precursor ions are produced;
comparing the mass to charge ratio and/or intensity profiles of the fragment ions with previously acquired data or with in-silico model data; and
determining the likely location of C=C double bonds (vinyl bonds) based on the comparison.

The lipid structure generally contains at least one alkyl chain.

The lipid molecules may comprise triglycerols, glycerophospholiids, sphingolipids, fatty acids, glycerolipids or saccharolipids.

According to another aspect there is provided a method of mass spectrometry comprising:
ionising lipid molecules to form a plurality of lipid parent ions;
subjecting the lipid parent ions to photon-induced fragmentation in order to cause the lipid parent ions to fragment to form a plurality of fragment or product ions;
mass analysing the fragment or product ions; and
determining the position of one or more unsaturated bonds in the lipid molecules by analysing an intensity profile of fragment or product ions that correspond with cleavage of carbon-carbon bonds from the end of a hydrocarbon chain of the lipid.

According to an embodiment the mass spectrometer may further comprise:
(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage may have an amplitude selected from the group consisting of: (i) < about 50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) > about 500 V peak to peak.

The AC or RF voltage may have a frequency selected from the group consisting of: (i) < about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) > about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) < about 0.0001 mbar; (ii) about 0.0001-0.001 mbar; (iii) about 0.001-0.01 mbar; (iv)

about 0.01-0.1 mbar; (v) about 0.1-1 mbar; (vi) about 1-10 mbar; (vii) about 10-100 mbar; (viii) about 100-1000 mbar; and (ix) > about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2 dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

BRIEF DESCRIPTION OF THE DRAWINGS

Various embodiments together with other arrangements given for illustrative purposes only will now be described, by way of example only, and with reference to the accompanying drawings in which.

DETAILED DESCRIPTION

A conventional approach to mass analysing lipids will first be discussed.

According to a conventional approach lipid molecules are ionised and are then subjected to Collision Induced Dissociation ("CID") by fragmenting the ions in the presence of a buffer gas.

Figure 1:
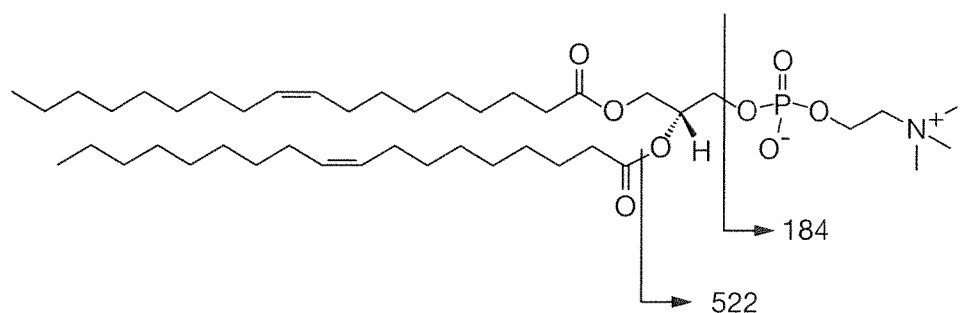
FIG. 1 shows a conventional Collisional Induced Dissociation mass spectrum obtained by fragmenting [M+H] parent ions of the phospholipid 1-2-dioleoyl-sn-glycero-3-phosphocholine in the presence of argon buffer gas.
Figure 1:
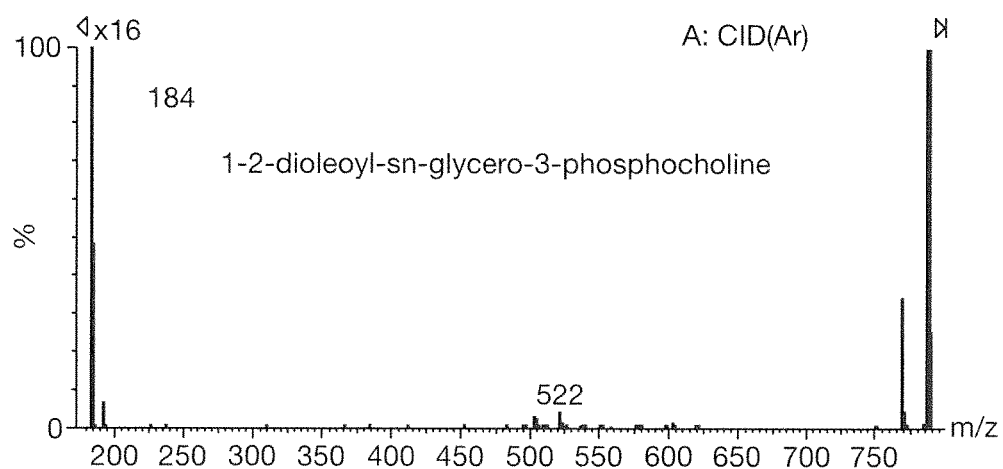

FIG. 1 shows a Collision Induced Dissociation mass spectrum obtained by fragmenting [M+H]$^+$ parent ions of 1-2-dioleoyl-sn-glycero-3-phosphocholine (a phospholipid) having a mass to charge ratio of 786.6 in the presence of argon buffer gas. The Collision Induced Dissociation mass spectrum is dominated by a large ion peak corresponding with fragment or product ions having a mass to charge ratio 184. Other less intense fragment or product ions having a mass to charge ratio of 552 are also observed.

FIG. 1 also shows the structure of the lipid molecule and indicates the bond cleavages that result in the formation of the fragment or product ions which are observed in the fragment or product ion spectrum shown in FIG. 1.

No information concerning the position of the unsaturated bonds within the molecule can be determined from the product ion mass spectrum shown in FIG. 1.

A first main embodiment will now be described. The embodiment relates to a method which advantageously enables the position of bonds within a molecule such as a lipid to be determined.

Figure 2:
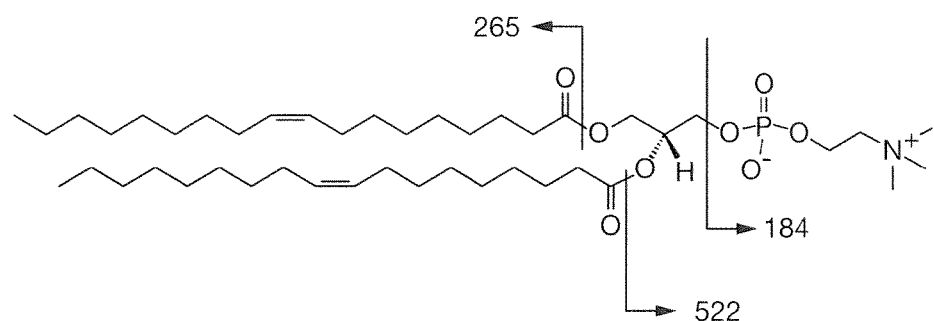
FIG. 2 shows a fragment or product ion mass spectrum according to an embodiment which was obtained by fragmenting [M+H] parent ions of 1-2-dioleoyl-sn-glycero-3-phosphocholine by irradiating the parent ions for approximately 1 second with UV light in the presence of oxygen buffer gas.
Figure 2:
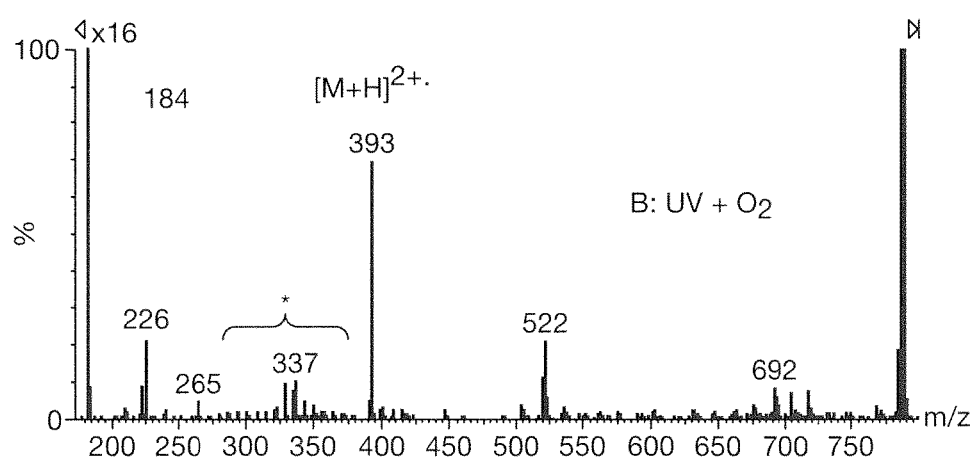

FIG. 2 shows a product ion spectrum of the same lipid parent ions as shown in FIG. 1 but wherein the parent lipid ions were irradiated for approximately 1 second with ultra-violet light in the presence of oxygen buffer gas. The process of irradiating the parent lipid ions with ultraviolet radiation causes the parent lipid ions to fragment. The parent or precursor lipid ions were trapped or confined in an RF confined ion guide and the lipid ions were directly illuminated using a commercial photoionisation lamp (Hamamatsu L10706). The photoionisation lamp emits a broad range of light of wavelength between 120 and 300 nm.

An advantageous feature of an embodiment is that the lipid parent ions may be photo-fragmented using an incoherent ultra-violet lamp rather than a more expensive laser.

The product ion spectrum as shown in FIG. 2 contains the same product or fragment ions having mass to charge ratios of 184 and 552 as are observed in a conventional Collision Induced Dissociation product ion spectrum as shown in FIG. 1. However, importantly, many other singly (and multiply) charged product or fragment ions are also observed.

The combination or intensity pattern of some of the product or fragment ions which are observed in the product ion spectrum obtained according to the techniques described herein allows or enables information such as the location of the unsaturated bonds in the hydrocarbon chains to be determined.

An important feature of the FIG. 2 spectrum is that a significant doubly charged radical precursor cation $[M+H]^{2+}$ having a mass to charge ratio of 393 is produced. This is in contrast to the conventional Collision Induced Dissociation approach as discussed above with reference to FIG. 1 wherein doubly charged radical cations having a mass to charge ratio of 393 are not observed.

Furthermore, an envelope of doubly charged product or fragment ions is produced which is of particular interest and is marked with an asterisk in FIG. 2.

The doubly charged product or fragment ions correspond with product or fragment ions which correspond with cleavage of C—C bonds from the hydrocarbon chains up to the position of the unsaturated bond. This suggests localization of charge due to electron detachment at the double bond.

Figure 3:
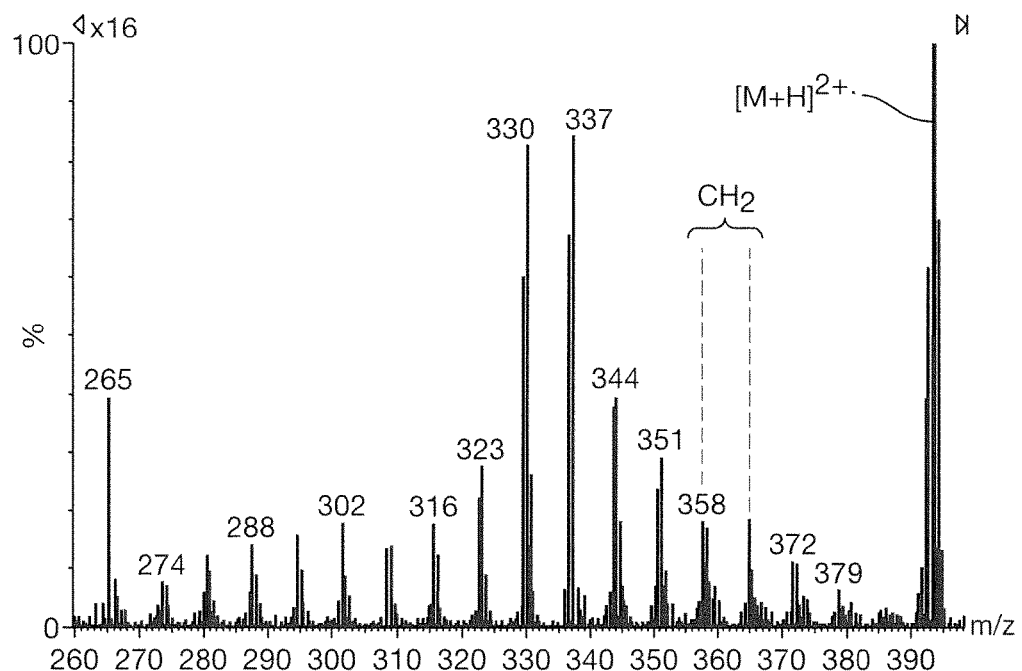
FIG. 3 shows in greater detail a region of the fragment or product ion mass spectrum shown in FIG. 2 and shows an intensity profile of characteristic doubly charged fragment or products ion wherein the intensity profile can then be compared against previously acquired or theoretically generated fragment or product ion intensity profiles in order to determine the location of carbon double bonds in the lipid molecules.

The envelope of doubly charged product or fragment ions which is marked with an asterisk in FIG. 2 is shown in more detail in FIG. 3.

The doubly charged product or fragment ions which are shown in FIG. 3 are due to loss of $CH_2$ subunits from the hydrocarbon chains. The intensity profile of the envelope of doubly charged product or fragment ions shown in FIG. 3 is indicative of the position of the double bonds on the hydrocarbon chain and enables the position of the double bonds on the hydrocarbon chain to be determined.

The presence of this envelope of characteristic doubly charged product or fragment ions may be explained by the differences in the mechanisms of dissociation between conventional Collisional Induced Dissociation and a radical ion driven process.

Collisional Induced Dissociation may be termed as being a slow dissociation process. In Collisional Induced Dissociation the energy transferred to the ions via collisions with the target gas has time to be distributed throughout the entire structure of the ion resulting in cleavage of the weakest bonds. In the case of the lipid shown in FIGS. 1 and 2 the probability of seeing losses from the hydrocarbon chain is very low and the C—O bond which is cleaved to produce product or fragment ions having a mass to charge ratio 184 has a low bond strength. Accordingly, there is a very high probability of the C—O bond breaking and hence ions having a mass to charge ratio of 184 being observed.

In contrast to conventional Collisional Induced Dissociation fragmentation processes, radical ion directed fragmentation may be considered as being a fast process and may result in bonds breaking in a substantially stochastic manner i.e. largely independent of bond strengths.

In addition to examining the intensity envelope of the doubly charged product ions from the alkyl chains, the radical precursor ion and/or higher charged product ions may be further excited by a second downstream fragmentation device such as a collision gas cell with or without isolation using a mass filter.

This increases the yield of informative fragmentation and produces extra informative fragmentation from the hydrocarbon chain which may be used to determine or confirm the probable structure of the hydrocarbon chain.

Two methods of using the intensity profile of the observed doubly charged product or fragment ions from the hydrocarbon chains to elucidate the structure of the lipids are discussed in more detail below.

Method 1

According to a first method a fragment ion spectra library of target lipids of known structure may be produced using the fragmentation method as described above.

Characteristic envelopes of fragment or product ions associated with losses from the hydrocarbon chain which are observed in the library of product or fragment ion mass spectra may then be compared with the envelope of fragment or product ions as produced by an unknown analyte ion.

A probability or score of correlation of the envelope of product or fragment ions within the library to that produced from the analyte may then be produced to indicate the likely structure of the hydrocarbon chain.

Various methods of matching the mass spectra may be used. For example, statistical methods such as principle component analysis ("PCA") or probabilistic or Bayesian methods may be used.

Method 2

According to a second method model or library data in-silico may be produced.

The method of assigning structure may comprise: (i) determining from the MS and MS-MS spectra the probable number and length of the hydrocarbon chains and possible number of C=C double bonds in the hydrocarbon chains. The type of lipid and nature of the polar head group may then be determined.

The method may further comprise: (ii) determining a set of possible structures for the target lipid for different unsaturated bond positions based on information obtained in step (i).

The method may then comprise: (iii) calculating predicted intensity envelopes for the product or fragment ions from losses from the hydrocarbon chains for the structures proposed in step (ii).

The method may then comprise: (iv) measuring the intensity envelope of product or fragment ions from losses from the hydrocarbon chain produced by photon induced electron detachment.

Finally, the method may further comprise: (v) comparing the measured fragmentation intensity envelope as obtained in step (iv) to the calculated envelopes for the possible subset of structures determined in step (iii) to determine the most probable position of the unsaturated bonds in each hydrocarbon chain.

The mass to charge ratio of the intact lipid and the nature of the polar head group may generally be known. In the example shown in FIG. 2 the product or fragment ions having a mass to charge ratio of 265, in conjunction with molecular ion mass to charge ratio value, indicates the length of the hydrocarbon chains and the total number of double bonds may be calculated.

The total width of the distribution of product or fragment ions also gives an indication of the range of structures which are possible. This narrows the set of calculated values required to fit to the data. In addition, Collision Induced Dissociation data may be used to confirm the basic structure of the lipid.

It has been shown for several molecules that fragmentation via the production of radical ions is substantially stochastic in nature (ETD, ECD). This results in relatively random probability of bond breakage as opposed to more deterministic slow fragmentation processes which generally result in cleavage of the weakest bonds.

This property may be used to construct a simple predictive model of the probability of observing mass losses from doubly charged radical cations due to cleavage of one or more C—C bonds.

For example, a lipid with two alkyl chains (chain 1 and chain 2) and with J and K breakable bonds respectively may be considered.

The probability of breaking an individual bond at position j on chain 1=p1j and the probability of breaking an individual bond at position k on chain 2=p2k.

Figure 4:
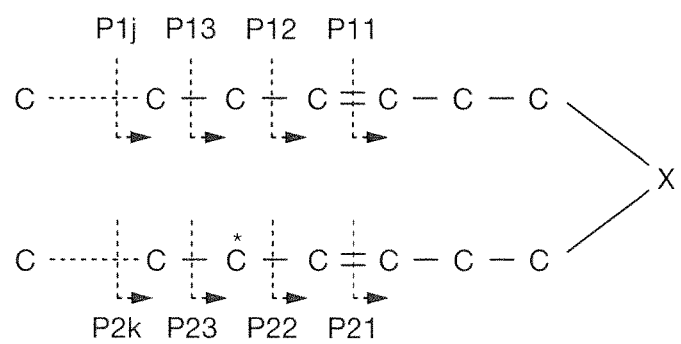
FIG. 4 shows a diagram representing the general structure of a lipid with two alkyl chains (chain 1 and chain 2) and with J and K breakable bonds respectively.

A diagram representing this general structure is shown in FIG. 4.

Each doubly charged fragment ion observed at lower mass to charge ratios than that of the doubly charged radical precursor ion corresponds to the loss of "n" alkyl groups from chain 1 and or "m" alkyl groups from chain 2.

The total number of alkyl groups lost is N wherein N=n+m.

The probability of seeing a loss of N alkyl groups Pr(N) is given by:

$$Pr(N) = \sum_{n+m=N, 0 \leq n \leq J, 0 \leq m \leq K} P_{nm} \quad (1)$$

wherein:

$$P_{nm} = p1(J-n+1)p2(K-m+1)\prod_{j=1}^{J-n}(1-p1j)\prod_{k=1}^{K-m}(1-p2k) \quad (2)$$

wherein:

$$p1(J+1) = 1 \quad (3)$$

$$p2(K+1) = 1 \quad (4)$$

Figure 5:
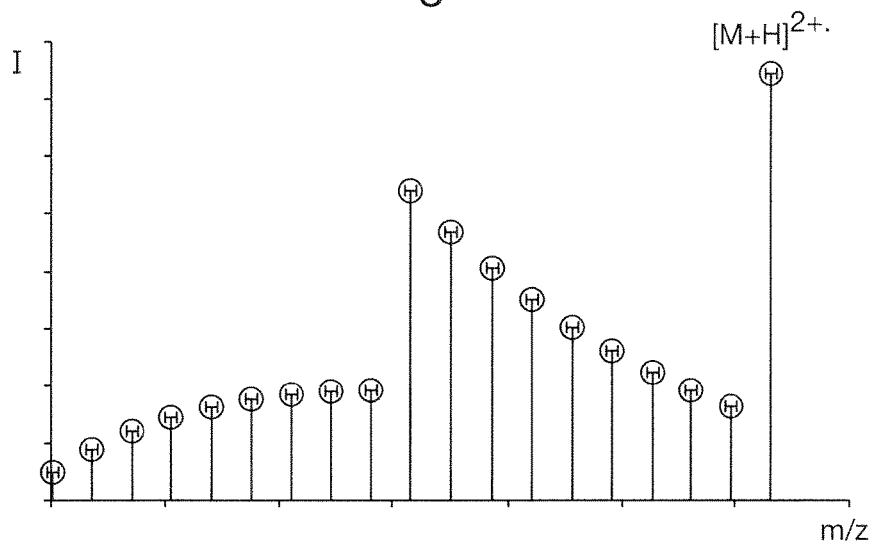
FIG. 5 shows a predicted intensity profile of fragment ions with p1j and p2k=0.1.

Using this simple model with p1j and p2k=0.1 and using the same lengths and structures of hydrocarbon chains as that shown in FIGS. 2 and 3 gives predicted intensities for the fragment ions as shown in FIG. 5.

The general form of the fragmentation envelope produced is very similar to the form observed in the data indicating that to at least a first approximation the fragmentation is indeed stochastic. Variations from this distribution are due to variations in probability of cleavage at certain bonds related to bond strengths.

For a given lipid structure the relative bond strengths of each of the C—C bonds in the hydrocarbon chain may be estimated. Molecular modelling software such as GAUSSIAN® may be used to determine the relative bond lengths or bond strengths to produce a value corresponding to the relative probability of a C—C bond breaking.

Differences in bond strength are likely to vary particularly in close proximity to a vinyl or unsaturated double bond. It is known that bond strengths in the vicinity of the allylic carbon (adjacent to the double bond) are generally weaker. This fact is exploited in organic synthesis reactions.

Figure 6:
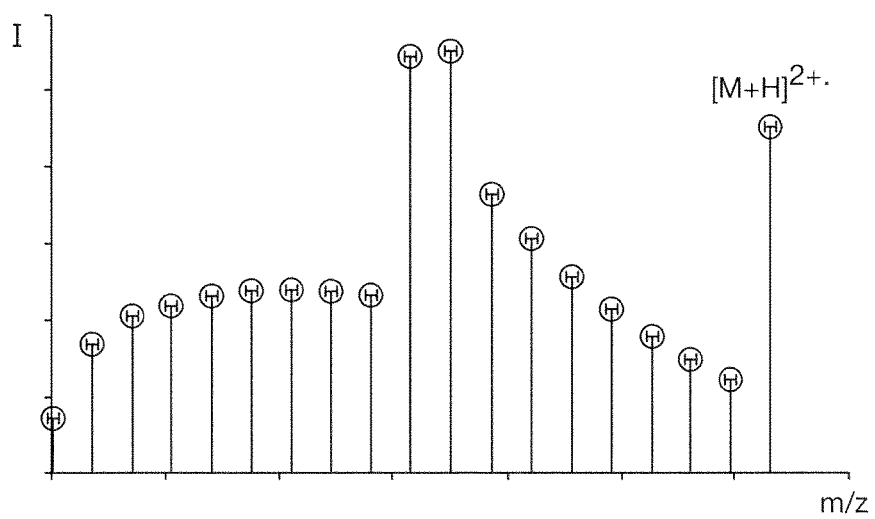
FIG. 6 shows a predicted intensity profile of fragment ions with p1j and p2k=0.12 for all bonds except the allylic carbon bond.

Assuming p1j and p2j equal 0.12 for all bonds except for the allylic carbon bond (C—C bond next to the double bond) which is given a probability of 0.16 results in a fragmentation envelope as shown in FIG. 6. This has features closer to the profile observed in the data shown in FIGS. 2 and 3.

By refining the relative probabilities in this basic model the form of the fragmentation profile may be approximated. Relatively small changes in the position of the double bond can make significant differences in the predicted fragmentation envelope.

Figure 7:
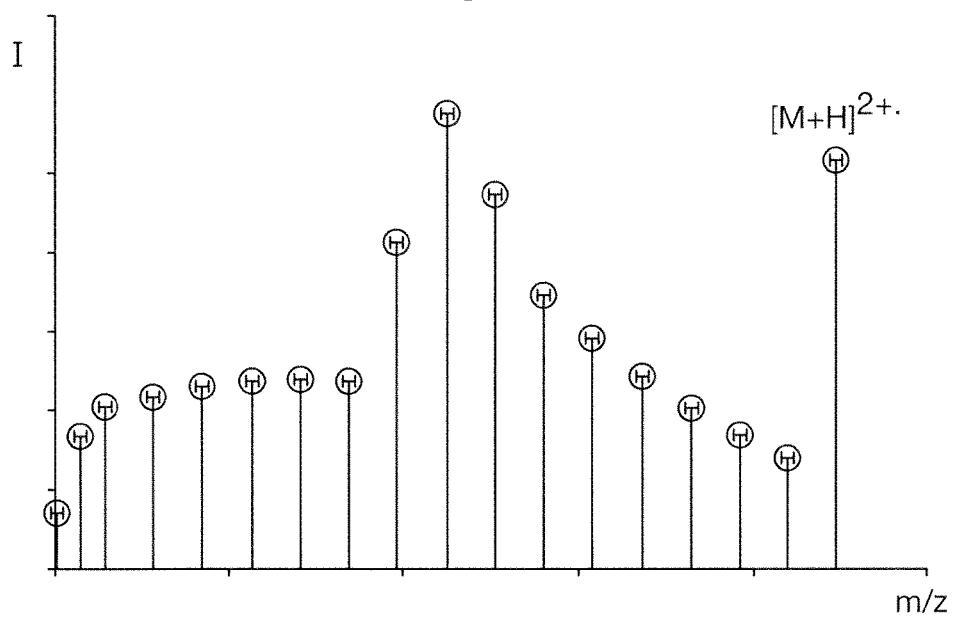
FIG. 7 shows a predicted intensity profile if one less $CH_2$ group is modelled on one of the chains.

For example, if one less $CH_2$ group is modelled on one of the chains in the example above, then an intensity envelope as shown in FIG. 7 is predicted. This pattern is indicative of the relative position of the double bond in each chain and may be used to localize the double bonds.

Many permutations of chain length and branching and double bond position may be calculated.

The probability of each bond cleaving may be further refined by examining and fitting predicted data to data from known model compounds with known structure.

In fitting the intensity envelope observed in the data to model data it is important to take into account instrumentation effects which may lead to a bias in the intensity profile with mass to charge ratio and or charge state. For example, the effective duty cycle of ion sampling in the pusher region of an orthogonal Time of Flight mass spectrometer is proportional to the square root of mass to charge ratio. If the ratio of singly and doubly charged product ions is theoretically modelled then the response of the ion detector to ions of differing charge state should optionally also be taken into account.

A second main embodiment will now be described. In this embodiment, the fragment or product ions formed by the methods described herein may be separated by ion mobility prior to mass analysis to produce a two dimensional mass vs. drift time plot.

A suitable apparatus for performing this experiment may comprise an ion source, with precursor ions formed in the ion source being subjected to high energy VUV light in an RF confined ion guide or ion trapping region. The high energy VUV light may cause the precursor ions to undergo electron photo detachment as described above to form a doubly charged radical precursor ion. The trapping region may be an RF only pre-filter region an analytical quadrupole.

The doubly charged radical ion may then optionally be selected using a quadrupole mass filter. Selecting this radical ion may result in an advantageous simplification of the final product ion spectrum as any background ions can be removed.

It is also contemplated that ions may be trapped within the analytical quadrupole and irradiated with VUV light within the quadrupole. Further mass isolation of the radical ion may be achieved by application of a resolving DC potential or by application of suitable supplementary excitation waveforms.

The mass selected radical ion may then be further activated to form further product or fragment ions. For instance, the mass selected radical ion may be accelerated into a collision gas cell to undergo collisional induced dissociation. These product ions may then be accumulated and periodically released into an ion mobility separation device. The product ions are thus separated according to ion mobility prior to their mass analysis e.g. in an orthogonal TOF mass analyser.

Optionally, ions exiting the ion mobility separation device may be activated again, e.g. in a further collision gas cell, to form second generation product ions prior to mass analysis.

Cleavages of the radical precursor ion at several different bond positions (e.g. on different alkyl chains) may give rise to multiple product ions having the same mass to charge value. The probability of producing a particular mass to charge value product ion, considering the different fragmentation pathways available, results in the characteristic product ion intensity envelope described above. These different product ions although indistinguishable by mass alone are significantly different in structure and hence different in interaction cross section so that they can be separated by ion mobility. The ion mobility drift times can be used in addition to the mass values and the intensity profile to provide further structural information to identify the analyte molecule.

The two methods of using the intensity profile discussed above may be extended to use this drift time or interaction cross section information.

For instance, in method 1 the drift time or calibrated cross section values may be stored in the library along with the mass and intensity information. In method 2, estimated cross sections for both precursor and product ions may be calculated in silico and used in addition to the calculated mass and product ion intensity values.

Three dimensional gas phase structures may be calculated for ions formed from this compound. Molecular mechanics and quantum chemistry modelling approaches are commonly employed for this purpose. For instance, software such as Gaussian (www.gaussian.com) is commercially available for these calculations. From these structures it is possible to calculate collision cross sections using software such as MobCal from Indiana University (A. A. Shvartsburg and M. F. Jarrold "An Exact Hard Spheres Scattering Model for the Mobilities of Polyatomic Ions", Chem. Phys. Lett. 1996, 261, 86-91).

The effect of long range electronic interactions between ions and polar or polarisable molecules in the IMS drift gas may on apparent collision cross section may also be taken into account with these calculations (Mesleh et al. "Structural Information from Ion Mobility Measurements: Effects of the Long-Range Potential", J. Phys. Chem. 1996, 100, 16082-16086).

As part of these calculations it may be necessary to obtain cross sections that have been thermally averaged (e.g. to account for internal movement of the ions in the gas phase).

Where it is not possible to obtain precise theoretical predictions, and a structure does not exist in a library, it may still be possible to correlate patterns in the two-dimensional data with structural details such as the number and positions of double bonds and the number and lengths of lipid chains.

The addition of the second dimension of IMS separation for the product ions produces a three dimensional pattern, mass to charge ratio, intensity and drift time (or collision cross section) which is very specific for the lipid type and the position and number of unsaturated bonds in the ion. Combining the methods described with ion mobility separation increases the confidence in the assignment of the structure of the compound analysed.

It should be noted that reduction of the mass to charge ratio, IMS data to mass to charge ratio and drift time pairs for individual mass to charge ratio peaks is not necessary or in some cases desirable to compare the two three dimensional (mass to charge ratio, intensity and drift time) data to library data or in silico modelled data. Comparing the raw mass to charge ratio drift time image data prior to any feature or component identification or post processing allows features such as IMS peak broadening or tailing or other shape information to be matched to the same features measured or modelled during building of the library data.

Localisation of other groups of molecules containing double bonds within hydrocarbon chains may be investigated by the techniques described above. For example, other embodiments are contemplated wherein the molecules which are analysed comprise hydrocarbons, vegetable oils, fatty acids, fatty aldehydes or ketones.

Other peaks in the spectrum may be used to give information about the length of the hydrocarbon chain of chains and the probable number of double bonds to add to the confidence in assignment. Different fragmentation methods may be combined to give the maximum structural information.

The intensities of fragment ions may be summed or binned within mass to charge ratio regions corresponding to the loss of carbon subunits and different number of hydrogen atoms. This results in the envelope of fragment ions seen for each nominal $CH_2$ loss appearing as a single intensity value. These intensity values may then be compared with simplified model data comparing the general form of the intensity envelope of the fragment ions to the model data or previously acquired library treated in the same way.

The method of predicting the intensity of fragments may be applied to fragmentation by other radical directed processes such as Electron Transfer Dissociation ("ETD"), Electron Capture Dissociation ("ECD") and metastable atom dissociation ("MAD").

Although the present invention has been described with reference to particular embodiments, it will be understood by those skilled in the art that various changes in form and detail may be made without departing from the scope of the invention as set forth in the accompanying claims.

The invention claimed is:

1. A method of mass spectrometry comprising:
ionising lipid molecules to form a plurality of lipid parent ions;
subjecting said lipid parent ions to photon-induced fragmentation in order to cause said lipid parent ions to fragment to form a plurality of fragment or product ions;
mass analysing said fragment or product ions, wherein subjecting said lipid parent ions to photon-induced fragmentation causes said lipid parent ions to fragment directly or indirectly; and
determining the position of one or more unsaturated bonds in said lipid molecules by analysing an intensity profile of fragment or product ions that correspond with cleavage of carbon-carbon bonds from the end of a hydrocarbon chain of the lipid up to the position of an unsaturated bond within said chain, wherein analysing said intensity profile of said fragment or product ions in order to determine the position of one or more unsaturated bonds in said lipid molecules comprises comparing said intensity profile to one or more previous experimentally obtained intensity profiles or comparing said intensity profile to a predicted, calculated or theoretical intensity profile.

2. A method as claimed in claim 1, wherein said fragment or product ions are multiply or substantially doubly charged.

3. A method as claimed in claim 1, wherein the step of subjecting said lipid parent ions to photon-induced fragmentation comprises directing photons emitted from an incoherent light source or non-laser light source onto said lipid parent ions.

4. A method as claimed in claim 1, wherein said lipid parent ions are caused to fragment via photon induced electron detachment.

5. A method as claimed in claim 1, wherein said lipid molecules comprise one or more triglycerols, glycerophospholiids, sphingolipids, fatty acids, glycerolipids or saccharolipids.

6. A method as claimed in claim 1, further comprising confining said lipid parent ions in an ion guide whilst subjecting said lipid parent ions to photon-induced fragmentation.

7. A method as claimed in claim 1, wherein said lipid parent ions comprise a first charge state and wherein said fragment or product ions comprise a second different charge state or comprise a second charge state that is a higher positive charge state or more positive than said first charge state.

8. A method as claimed in claim 1, wherein said lipid parent ions are substantially singly charged.

9. A method as claimed in claim 1, wherein the step of subjecting said lipid parent ions to photon-induced fragmentation causes said lipid parent ions to fragment by photon induced electron detachment, photodissociation or photoactivation.

10. A method as claimed in claim 1, further comprising causing at least some of said lipid parent ions to interact with excited neutral gas molecules or causing at least some of said lipid parent ions to form radical ions and/or metastable ions.

11. A method as claimed in claim 10, wherein said radical ions or metastable ions subsequently dissociate to form said fragment or product ions.

12. A method as claimed in claim 1, wherein the step of subjecting said lipid parent ions to photon-induced fragmentation comprises subjecting said lipid parent ions to ultraviolet radiation.

13. A method as claimed in claim 1, wherein the step of subjecting said lipid parent ions to photon-induced fragmentation comprises directing photons emitted from a vacuum ultraviolet ("VUV") discharge lamp, a glow discharge lamp, an ultraviolet lamp, a lamp onto said lipid parent ions.

14. A method as claimed in claim 1, wherein the step of analysing said intensity profile of said fragment or product ions in order to determine the position of one or more bonds in said lipid molecules comprises determining the position of one or more C=C double bonds, carbon double bonds or vinyl bonds in said lipid molecules.

15. A method as claimed in claim 1, further comprising subjecting at least some of said lipid parent ions or said plurality of fragment or product ions to supplementary activation to form a plurality of further fragment or product ions and mass analysing said further fragment or product ions.

16. A method as claimed in claim 15, further comprising selecting by mass or using a mass filter one or more of said lipid parent ions or one or more ions derived from said lipid parent ions prior to the step of supplementary activation.

17. A method as claimed in claim 1, further comprising separating at least some of said lipid parent ions, at least some ions derived from said lipid parent ions or at least some fragment or product ions according to ion mobility prior to mass analysis.

18. A mass spectrometer comprising:
an ion source arranged and adapted to ionise lipid molecules to form a plurality of lipid parent ions;
a photon-induced fragmentation device arranged and adapted to subject said lipid parent ions to photon-induced fragmentation in order to cause said lipid parent ions to fragment to form a plurality of fragment or product ions, wherein subjecting said lipid parent ions to photon-induced fragmentation causes said lipid parent ions to fragment directly or indirectly;
a mass analyser arranged and adapted to mass analyse said fragment or product ions; and
a control system arranged and adapted to determine the position of one or more unsaturated bonds in said lipid molecules by analysing an intensity profile of fragment or product ions that correspond with cleavage of carbon-carbon bonds from the end of a hydrocarbon chain of the lipid up to the position of an unsaturated bond within said chain, wherein analysing said intensity profile of said fragment or product ions in order to determine the position of one or more unsaturated bonds in said lipid molecules comprises comparing said intensity profile to one or more previous experimentally obtained intensity profiles or comparing said intensity profile to a predicted, calculated or theoretical intensity profile.

* * * * *